United States Patent [19]

Henneberger et al.

[11] Patent Number: 5,438,138

[45] Date of Patent: Aug. 1, 1995

[54] PROCESS FOR THE PREPARATION OF MONO- AND DIARYLTRIAZINES

[75] Inventors: Helmut Henneberger, Rheinfelden, Germany; Markus Wagner, Füllinsdorf, Switzerland

[73] Assignee: Ciba-Geigy Corporation, Ardsley, N.Y.

[21] Appl. No.: 83,960

[22] Filed: Jun. 28, 1993

[30] Foreign Application Priority Data

Jul. 2, 1992 [CH] Switzerland .................... 2086/92

[51] Int. Cl.$^6$ .................. C07D 251/22; C07D 251/20
[52] U.S. Cl. .................................................. 544/217
[58] Field of Search .......................................... 544/217

[56] References Cited

U.S. PATENT DOCUMENTS

| | | | |
|---|---|---|---|
| 3,118,887 | 1/1964 | Hardy et al. | 260/248 |
| 3,244,708 | 4/1966 | Duennanberger et al. | 260/248 |
| 3,268,474 | 8/1966 | Hardy et al. | 260/458 |
| 3,268,528 | 8/1966 | Bader et al. | 260/248 |
| 4,092,466 | 5/1978 | Fletcher et al. | 526/13 |

OTHER PUBLICATIONS

Ostrogovich, Chem.-Ztg. 78, 738 (1912).
Hirt et al., Helo. Chim. Acta 178-9, 1365 (1950).
C.A. 46:120d-121c (1952).
H. Bader, et al. J. Org. Chem. 30, 702-7 (1965).

Primary Examiner—John M. Ford
Attorney, Agent, or Firm—Luther A. R. Hall

[57] ABSTRACT

A process for the selective preparation of 2,4-dichloro-6-aryl- or 2-chloro-4,6-diaryl-1,3,5-triazines is described, which comprises reacting a compound of formula II

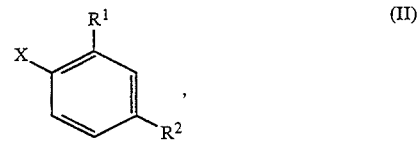

wherein X is a bromine or chlorine atom, and $R^1$ and $R^2$ are independently hydrogen or alkyl, in tetrahydrofuran with magnesium metal to form the corresponding Grignard reagent, and reacting the resultant solution with cyanuric chloride of formula III

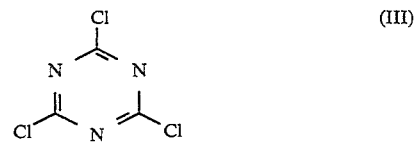

such that, if Z is —Cl, at least 1.05 mol and, if Z is a radical of formula Ib, at least 2.1 mol, of Grignard reagent is used per 1 mol of cyanuric chloride. The compounds of formula I can be used with advantage for the preparation of 2-(o-hydroxyphenyl)-4,6-diaryl-s-triazines, which are known light stabilizers for organic material.

15 Claims, No Drawings

PROCESS FOR THE PREPARATION OF MONO- AND DIARYLTRIAZINES

The present invention relates to a process for the selective preparation of 2,4-dichloro-6-aryl- or 2-chloro-4,6-diaryl-1,3,5-triazines from cyanuric chloride and arylmagnesium halides.

Triaryltriazines are obtainable, intere alia, by reacting benzamides with resorcinol derivatives with formation of the triazine ring (U.S. Pat. No. 3,268,474). Other syntheses start from cyanuric halides which are reacted with phenyl derivatives by Friedel-Craft or Grignard reactions (q.v. inter alia U.S. Pat. No. 3,244,708). A good overview of different synthesis methods is given by, inter alia, E. M. Smolin and L. Rapoport, "s-Triazines and Derivatives," Interscience Publishers Inc., New York 1959, and also in U.S. Pat. No. 3,268,474 and U.S. Pat. No. 3,118,887.

The substitution of 1 or 2 chlorine atoms of the cyanuric chloride by phenyl by means of a Grignard reaction has already been described by A. Ostrogovich, Chemiker-Zeitung No. 78,738 (1912), and Hirt et al., *Helv. Chim. Acta* 178–179, 1365 (1950).

The synthesis of 2-chloro-4,6-dialkyl-1,3,5-triazine by Grignard reactions at a temperature of $-15°$ C. is described in U.S. Pat. No. 3,268,528 and by Bader et al., *J. Org. Chem.* 30, 702 (1965). Bader et al. investigate the influence of different solvents on the yield and the type of by-products obtained. They observe an accelerated substitution of chlorine and an increase in the number of side-reactions when using tetrahydrofuran.

U.S. Pat. No. 4,092,466 discloses a method of synthesising 2-chloro-4,6-diphenyl-1,3,5-triazine, which comprises first preparing the Grignard solution in conventional manner from bromobenzene and magnesium in diethyl ether, then combining this solution with a solution of cyanuric chloride in benzene and reacting the mixture at 4°–15° C. to give the crude product.

A common feature of both known processes for the selective substitution of 1 or 2 chlorine atoms of the cyanuric chloride is the formation of a large number of unwanted by-products.

Surprisingly, it has now been found that cyanuric chloride can be reacted selectively with arylmagnesium halides dissolved in tetrahydrofuran to give a high yield of 2,4-dichloro-aryl-1,3,5-triazines or selectively to 2-chloro-4,6-diaryl-1,3,5-triazines. Accordingly, the invention relates to a process for the preparation of a single compound of formula Ia

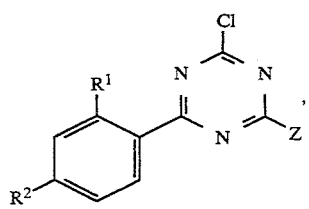

wherein $R^1$ and $R^2$ are each independently of the other hydrogen or $C_1$–$C_4$alkyl, and Z is a radical of formula Ib

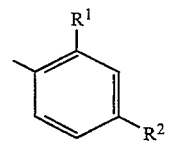

or —Cl, which comprises reacting a compound of formula II

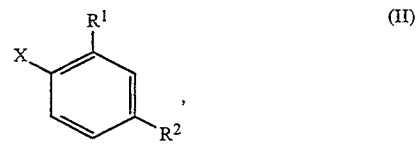

wherein X is a bromine or chlorine atom, and $R^1$ and $R^2$ are as defined above, in tetrahydrofuran with magnesium metal to form the corresponding Grignard reagent, and reacting the resultant solution with cyanuric chloride of formula III

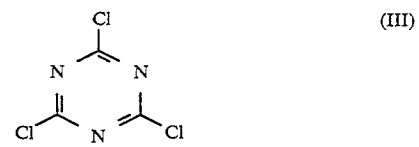

such that, if Z is —Cl, at least 1.05 mol and, if Z is a radical of formula Ib, at least 2.1 mol, of the Grignard reagent is used per 1 mol of cyanuric chloride.

A preferred embodiment of the invention is a process for the preparation of 2-chloro-4,6-diaryl-1,3,5-triazines of formula I,

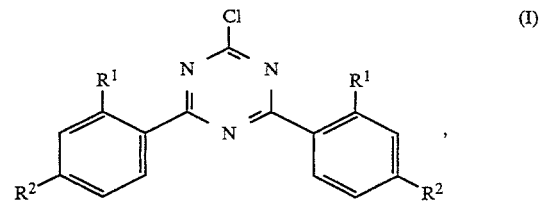

wherein $R^1$ and $R^2$ are each independently of the other hydrogen or $C_1$–$C_4$alkyl, which comprises reacting a compound of formula II

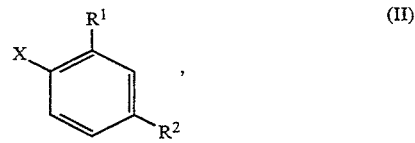

wherein X is a bromine or chlorine atom, and $R^1$ and $R^2$ are as defined above, in tetrahydrofuran with magnesium metal to form the corresponding Grignard reagent, and reacting the resultant solution with cyanuric chloride of formula III

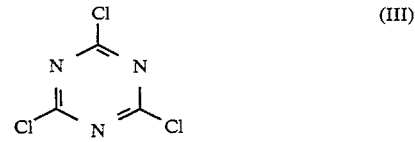

such that at least 2.1 mol of the Grignard reagent is used per 1 mol of cyanuric chloride.

The reaction product of the compound of formula II with magnesium metal is known to those skilled in the art as a Grignard reagent. Other than tetrahydrofuran (THF), no further solvent is present in the preparation of the Grignard reagent in the inventive process.

A process in which no solvent other than tetrahydrofuran (THF) is used even in the reaction with cyanuric chloride constitutes a preferred embodiment of the invention. In this case, cyanuric chloride is preferably dissolved in tetrahydrofuran and this solution is then combined with the solution of the Grignard reagent.

It is also possible to use another solvent in addition to tetrahydrofuran in the reaction with cyanuric chloride. Suitable additional solvents include acyclic or other cyclic ethers or aromatic or aliphatic hydrocarbons. It is preferred to use dioxane, toluene, xylene, hexane, cyclohexane, petroleum ether or mixtures of these solvents, most preferably toluene. In this case, it is best to charge cyanuric chloride as solution in the additional solvent to the reactor and to add the solution of the Grignard reagent thereto.

A process which comprises charging cyanuric chloride to the reactor as solution in tetrahydrofuran, toluene or a mixture of toluene and tetrahydrofuran, and then adding the Grignard reagent as solution in tetrahydrofuran, likewise constitutes a preferred embodiment of the invention.

The concentration of cyanuric chloride charged to the reactor is preferably 1 to 3 mol per liter of solvent.

The reaction time depends on a number of parameters, for example the type of substituent Z (product mono- or diarylated), the type of substituents of the Grignard reagent X, $R^1$ und $R^2$, and the chosen temperature. The total reaction time is usually from 1 to 24 hours, including the time taken for the addition of the solution of the Grignard reagent, which is from 0.5 to 3 hours. The reaction time for reacting Grignard reagents obtained from educts of formula II, wherein $R^1$=H, is from 1 to 6, preferably from 2 to 5, hours.

The reaction mixture will preferably be stirred during the mixing of the Grignard reagent and cyanuric chloride as well as during the entire reaction time, and kept in the temperature range from $-5°$ C. to $+45°$ C., conveniently in the temperature range from $-5°$ C. to $+30°$ C., preferably from 0° C. to 25° C., most preferably from 5° C. to 20° C.

The Grignard reagent is preferably used in a 10 to 100% stoichiometric excess, so that, if Z is —Cl, 1.1. to 2 mol and, if Z is a radical of formula Ib, conveniently 2.2. to 4 mol, of Grignard reagent is used per 1 mol of cyanuric chloride. Normally the excess is 10 to 75%. Preferably the excess is 25 to 50%, i.e. if Z is —Cl, 1.25 to 1.5 mol and, if Z is a radical of formula Ib, preferably 2.5 to 3 mol, of Grignard reagent is used per 1 mol of cyanuric chloride.

A homogeneous educt of formula II, wherein X=Br or X=Cl, can be used to prepare the Grignard reagent. It is, however, also possible to use mixtures of bromine and chlorine compounds.

The degree of reaction is expediently followed during the reaction by analysing samples of the reaction mixture. Analysis may be made by thin-layer chromatography.

Working up of the reaction mixture can be effected in known manner, typically by dilution with a nonpolar organic solvent, hydrolysis of the excess Grignard reagent, and separating, washing and drying the organic phase and removing the solvent. Suitable diluents include aliphatic or aromatic hydrocarbons such as petroleum ether, toluene or xylene. Toluene is especially preferred. Hydrolysis of the unreacted Grignard reagent is preferably effected by addition of a sufficient amount of dilute mineral acid, typically 0.1 to 5 molar aqueous HCl. It is advantageous to use an excess of acid for the hydrolysis, typically 2 to 5 mol of aqueous HCl per 1 mol of unreacted Grignard reagent.

The process product, the compound of formula Ia or the compound of formula I, is obtained in high purity as single compound, so that purification by distillation can usefully be dispensed with. An optional further purification can be carried out by recrystallisation. Those skilled in the art will be familiar with suitable solvents therefor, typically nonpolar organic solvents such as aliphatic or aromatic hydrocarbons, alcohols, amides or ethers. Alcohols which may suitably be used are $C_3$–$C_5$ alcohols such as 2-butanol.

The Grignard reagent used in the novel process is dissolved in tetrahydrofuran without the addition of another solvent. The preparation of the Grignard reagent in tetrahydrofuran can be carried out in known manner. Typically, magnesium metal in suitable form such as turnings, powder or strips, is first activated. This can be done by briefly heating the magnesium in THF; but it is also possible to add a catalytic amount of an activator such as iodine. The compound of formula II is then added in about equivalent amount or in up to about 10% molar excess, conveniently as solution in THF. If a compound of formula II, wherein X is a chlorine atom, is used, it can be advantageous to add an additional minor amount of the corresponding bromine compound, typically 1 to 10% by weight, based on the chlorine compound. The ensuing reaction is exothermic, or the mixture is warmed to a temperature in the range from c. 25° C. to the boiling point of the THF, preferably to reflux temperature. It is expedient to continue the reaction until the magnesium is completely dissolved. The amount of solvent is preferably calculated such that 3 to 3.5 mol of tetrahydrofuran is used per 1 mol of Grignard reagent.

Compounds of formula II, wherein X is a chlorine atom, are of particular interest for use in the inventive process.

$R^1$ and $R^2$ defined as $C_1$–$C_4$alkyl are methyl, ethyl, 1-propyl (n-propyl), 2-propyl (isopropyl), 1-butyl(n-butyl), 2-butyl (sec-butyl), 2-methylpropyl (isobutyl) or 1,1-dimethylethyl (tert-butyl). Methyl or tert-butyl are preferred.

Preferably $R^1$ is hydrogen or methyl and $R^2$ is hydrogen or $C_1$–$C_4$alkyl. Most preferably, $R^1$ and $R^2$ are each independently of the other hydrogen or methyl. In a particularly preferred embodiment of the invention, the compound of formula II is chlorobenzene, bromobenzene, 4-chlorotoluene, 4-bromotoluene, 2,4-dimethylbromobenzene or 2,4-dimethylchlorobenzene.

Accordingly, a particularly preferred emodiment of the invention relates to a process which comprises charging cyanuric chloride as solution in tetrahydrofuran, toluene or a mixture of toluene and tetrahydrofuran to the reactor and, with stirring and cooling, adding a solution of 2.5 to 3 mol of the reaction product of chlorobenzene, bromobenzene, 4-chlorotoluene, 4-bromotoluene, 2,4-dimethylbromobenzene or 2,4-dimethylchlorobenzene with magnesium in tetrahydrofuran.

The compounds of formula Ia or I can be used with advantage for the synthesis of 2-(o-hydroxyphenyl)-4,6-diaryl-s-triazines which are known light stabilisers for organic material. Examples of the use of these compounds will be found, inter alia, in U.S. Pat. No. 3,244,708.

The following Examples illustrate the novel process in more detail. Unless otherwise indicated, all parts and percentages are by weight.

EXAMPLE 1

Preparation of 2-chloro-4,6-diphenyl-1,3,5-triazine 24.30 g (1.0 mol) of iodine-activated magnesium turnings in 40 ml of anhydrous tetrahydrofuran (THF) are heated briefly to c. 60° C. Then 157.0 g (1.0 mol) of bromobenzene and 220 ml of THF are added dropwise over 30 min and the reaction mixture is therafter kept for 2 hours at reflux temperature. After cooling, the Grignard solution is added over 2 hours to a mixture of 61.4 g (0.33 mol) of cyanuric chloride and 215 ml of THF, while keeping the temperature of the mixture in the range from 0° to 20° C. When the addition is complete, the mixture is stirred for a further hour at 20° C. At this time, a thin-layer chromatogram (eluant:toluene:hexane=1:1) shows that no more monoaryltriazine is detectable.

Afterwards, the mixture is diluted with 300 ml of toluene, the resultant suspension is poured into 316 g of 12% aqueous HCl, the organic phase is separated, washed with a total amount of 400 g of water and concentrated. The resultant material (melting point 128°–134° C.) contains 92% of the title compound (yield: 99.5% of theory). Recrystallisation from 2-butanol gives the title compound of melting point 136°–139° C. Analysis $C_{15}H_{10}ClN_3$: calcd 67.30% C; 3.76% H; 15.70% N; 13.24% Cl; found 67.15% C; 3.88% H; 15.69% N; 13.12% Cl.

EXAMPLE 2

Preparation of 2-chloro-4,6-diphenyl-1,3,5-triazine 24.3 g (1.0 mol) of iodine-activated magnesium turnings in 40 ml of anhydrous THF are heated briefly to c. 60° C. Then 113.1 g (1.0 mol) of chlorobenzene and additionally c. 4% of bromobenzene as well as 220 ml of THF are added dropwise over 50 min and the mixture is kept for 2.5 hours at reflux temperature. After cooling, the Grignard solution is added over 2 hours to a mixture of 68.2 g (0.37 mol) of cyanuric chloride and 215 ml of THF, while keeping the temperature of the mixture in the range from 0° to 15° C. When the addition is complete, the mixture is stirred at 15° C. until a thin-layer chromatogram (eluant:toluene:hexane =1:1) shows that no more monoaryltriazine is detectable (after c. 2.5 hours).

The mixture is then diluted with 300 ml of toluene, the resultant suspension is poured into 316 g of 12% aqueous HCl, the organic phase is separated, washed with a total amount of 400 g of water and concentrated. The resultant material (melting range 118°–128° C.) contains 81% of the title compound. The yield is 81%.

EXAMPLE 3

Preparation of 2-chloro-4,6-di-(4-methylphenyl)-1,3,5-triazine 17.0 g (0.7 mol) of iodine-activated magnesium turnings in 40 ml of anhydrous THF are heated briefly to c. 60° C. Then 122.2 g (0.7 mol) of 1-bromo-4-methylbenzene and 140 ml of THF are added dropwise over 30 min and the mixture is kept for 2 hours at reflux temperature. After cooling, the Grignard solution is added over 1 hour to a mixture of 43.0 g (0.23 mol) of cyanuric chloride and 150 ml of THF, while keeping the temperature of the mixture in the range from 0° to 10° C. When the addition is complete, the mixture is stirred at 0°–15° C. until a thin-layer chromatogram (eluant:toluene:hexane=1:1) shows that no more monoaryltriazine is detectable (after c. 2.5 hours).

The mixture is then diluted with 210 ml of toluene, the resultant suspension is poured into 221 g of 12% aqueous HCl, the organic phase is separated, washed with a total amount of 280 g of water, concentrated, and the residue is purified with 486 g of 2-butanol. The resultant material (melting range 205°–206° C.) contains 99% of the title compound. The yield is 73%.

EXAMPLE 4

Preparation of 2-chloro-4,6-bis(2,4-dimethylphenyl)-1,3,5-triazine 24.3 g (1.0 mol) of iodine-activated magnesium turnings in 40 ml of anhydrous THF are heated briefly to c. 60° C. Then 221.2 g (1.0 mol) of 1-bromo-2,4-dimethylbenzene and 220 ml of THF are added dropwise over 60 min and the mixture is kept for 1.5 hours at reflux temperature. After cooling, the Grignard solution is added over 1.5 hours to a mixture of 61.5 g (0.33 mol) of cyanuric chloride and 215 ml of THF, while keeping the temperature of the mixture in the range from 0° to 5° C. When the addition is complete, the mixture is stirred at 5°–25° C. until a thin-layer chromatogram (eluant:toluene:hexane=1:1) shows that no more monoaryltriazine is detectable (after 20 hours).

The mixture is then diluted with 300 ml of toluene, the resultant suspension is poured into 316 g of 12% aqueous HCl, the organic phase is separated, washed with a total amount of 900 g of water and concentrated. The resultant material (melting point 135.5°–137° C.) contains 97.3% of the title compound. The yield is 72%.

EXAMPLE 5

Preparation of 2,4-dichloro-6-phenyl-1,3,5-triazine 7.80 g (0.32 mol) of iodine-activated magnesium turnings in 20 ml of anhydrous THF are heated briefly to 60° C. Then 47.1 g (0.30 mol) of bromobenzene and 80 ml of THF are added dropwise over 30 min and the mixture is heated for 1.5 hours to 65° C. After cooling, the Grignard solution is added over 1 hour to a mixture of 51.6 g (0.28 mol) of cyanuric chloride and 140 ml of THF, while keeping the temperature of the mixture in the range from 10° to 20° C. When the addition is complete, the mixture is stirred at for 3 hours at 25° C. The mixture is then diluted with 280 ml of toluene, the resultant suspension is poured into 300 g of 12% aqueous HCl, the organic phase is separated, washed with a total amount of 400 g of water and concentrated. The resultant material (melting point 117°–120° C.) is recrystalised from hexane, giving the title compound in a yield of 61%.

EXAMPLE 6

Preparation of 2,4-dichloro-6-(2,4-dimethylphenyl)-1,3,5-triazine 17.0 g (0.70 mol) of iodine-activated magnesium turnings in 25 ml of anhydrous THF are heated briefly to 60° C. Then 154.9 g (0.70 mol) of 4-bromo-m-xylene (in c. 90% purity) and 155 ml of THF are added dropwise over 30 min and the mixture is heated for 2 hours to reflux. After cooling, the Grignard solution is added over 1.5 hours to a mixture of 43.0 g (0.233 mol) of cyanuric chloride and 150 ml of THF, while keeping the temperature of the mixture in the range from 0° to 10° C. The mixture is then diluted with 210 ml of toluene, the resultant suspension is poured into 220 g of 12% aqueous HCl, the organic phase is separated, washed with a total amount of 280 g of water and concentrated. The resultant material is recrystallised from 2-butanol, giving the title compound with a melting point of 135.5°–137° C. in a yield of 79.8%.

What is claimed is:

1. A process for the preparation of a single compound of formula Ia

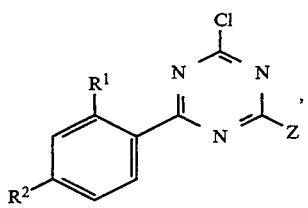

wherein $R^1$ and $R^2$ are each independently of the other hydrogen or $C_1$–$C_4$alkyl, and Z is a radical of formula Ib

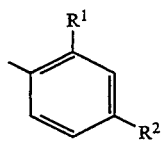

or —Cl, which comprises reacting a compound of formula II

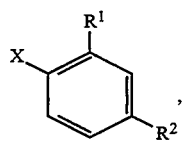

wherein X is a bromine or chlorine atom, and $R^1$ and $R^2$ are as defined above, in tetrahydrofuran with magnesium metal to form the corresponding Grignard reagent, and reacting the resultant solution with cyanuric chloride of formula III

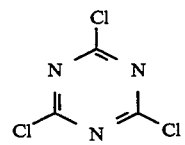

such that, when Z is —Cl, at least 1.05 mol or, when, Z is a radical of formula Ib, at least 2.1 mol, of the Grignard reagent is used per 1 mol of cyanuric chloride.

2. A process according to claim 1, wherein $R^1$ is hydrogen or methyl and $R^2$ is hydrogen or $C_1$–$C_4$alkyl.

3. A process according to claim 2, wherein $R^1$ and $R^2$ are each independently of the other hydrogen or methyl.

4. A process according to claim 1, wherein the compound of formula II is selected from the group consisting of chlorobenzene, bromobenzene, 4-chlorotoluene, 4-bromotoluene, 2,4-dimethylbromobenzene and 2,4-dimethylchlorobenzene.

5. A process according to claim 1, wherein the further purification of the compound of formula I is effected without distillation.

6. A process according to claim 1, wherein no solvent other than tetrahydrofuran is used.

7. A process according to claim 1, wherein a further solvent in addition to tetrahydrofuran is used for the reaction with cyanuric chloride.

8. A process according to claim 7, wherein the additional solvent is a further ether or an aliphatic or aromatic hydrocarbon or a mixture of said solvents.

9. A process according to claim 8, wherein the additional solvent is selected from the group consisting of dioxane, toluene, xylene, hexane, cyclohexane, petroleum ether or a mixture of said solvents.

10. A process according to claim 7, which comprises adding the solution of the Grignard reagent in tetrahydrofuran to a solution of cyanuric chloride in the additional solvent.

11. A process according to claim 1, wherein, when Z is —Cl, 1.1 to 2 mol or, when Z is a radical of formula Ib, 2.2. to 4 mol, of Grignard reagent is used per 1 mol of cyanuric chloride.

12. A process according to claim 11, wherein, when Z is —Cl, 1.25 to 1.5 mol or, when Z is a radical of formula Ib, 2.5 to 3 mol, of Grignard reagent is used per 1 mol of cyanuric chloride.

13. A process according to claim 1, wherein cyanuric chloride is charged to the reactor as solution in tetrahydrofuran, toluene or a mixture of toluene and tetrahydrofuran, and a solution of the Grignard reagent in tetrahydrofuran is added thereto.

14. A process according to claim 1, wherein the reaction mixture is kept during the reaction with cyanuric chloride in the temperature range from $-5°$ C. to $+45°$ C.

15. A process according to claim 1 for the preparation of a 2-chloro-4,6-diaryl-1,3,5-triazines of formula I,

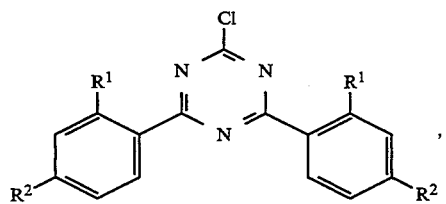

wherein $R^1$ and $R^2$ are each independently of the other hydrogen or $C_1$–$C_4$alkyl, which comprises reacting a compound of formula II

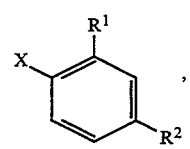

wherein X is a bromine or chlorine atom, and $R^1$ and $R^2$ are as defined above, in tetrahydrofuran with magnesium metal to form the corresponding Grignard reagent, and reacting the resultant solution with cyanuric chloride of formula III
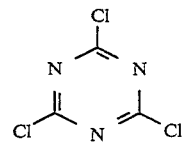
(III)
such that at least 2.1 mol of Grignard reagent is used per 1 mol of cyanuric chloride.
* * * * *